United States Patent [19]
Ribelin et al.

[11] Patent Number: 6,130,191
[45] Date of Patent: Oct. 10, 2000

[54] PROCESS FOR THE PREPARATION OF TRIMETHYLOLPROPANE CAPRYLATE/ CAPRATE

[75] Inventors: Robert P. Ribelin, Cincinnati; Stephen W. Turner, Hamilton, both of Ohio

[73] Assignee: Henkel Corporation, Gulph Mills, Pa.

[21] Appl. No.: 09/394,186

[22] Filed: Sep. 10, 1999

Related U.S. Application Data

[60] Provisional application No. 60/102,278, Sep. 29, 1998.
[51] Int. Cl.[7] .......................... C10M 105/38; C07C 67/02
[52] U.S. Cl. .......................... 508/485; 560/231; 560/234; 560/263
[58] Field of Search ............................. 508/485; 560/234

[56] References Cited

U.S. PATENT DOCUMENTS

| | | | |
|---|---|---|---|
| 4,655,947 | 4/1987 | Tsai et al. | 508/485 |
| 4,826,633 | 5/1989 | Carr et al. | 508/485 |
| 5,866,710 | 2/1999 | Ridland et al. | 560/231 |
| 5,885,946 | 3/1999 | Lamsa | 508/485 |
| 5,916,854 | 6/1999 | Inaya et al. | 508/485 |
| 5,922,657 | 7/1999 | Camenzind et al. | 508/430 |

*Primary Examiner*—Ellen M. McAvoy
*Attorney, Agent, or Firm*—John E. Drach; Henry E. Millson, Jr.

[57] ABSTRACT

A process for the preparation of a mixture of trimethylolpropane caprylate and trimethylolpropane caprate comprising the steps of A) purifying a less than pure mixture of methyl caprylate and methyl caprate;

B) reacting the purified mixture from step A) with trimethylolpropane to transesterify the purified mixture to produce a reaction mixture containing trimethylolpropane caprylate and trimethylolpropane caprate; and C) removing methanol and unreacted methyl caprylate and methyl caprate from the reaction mixture.

30 Claims, No Drawings

PROCESS FOR THE PREPARATION OF TRIMETHYLOLPROPANE CAPRYLATE/CAPRATE

CROSS-REFERENCE TO RELATED APPLICATIONS

This application claims priority of provisional application Ser. No. 60/102,278, filed on Sep. 29, 1998.

STATEMENT REGARDING FEDERALLY SPONSORED RESEARCH OR DEVELOPMENT

Not Applicable.

FIELD OF THE INVENTION

This invention relates to synthetic oils used as a base in motor oils, and to a new process for their preparation.

BACKGROUND OF THE INVENTION

Trimethylolpropane caprylate/caprate is currently used as a synthetic oil base for motor oils. This product is currently manufactured by the direct esterification of trimethylolpropane with a mixture of caprylic acid and capric acid using stannous oxylate as a catalyst.

SUMMARY OF THE INVENTION

It has now been discovered that trimethylolpropane caprylate/caprate can be prepared by transesterifying methyl caprylate/caprate with trimethylolpropane.

The process is carried out using the following steps:

a) purifying a less than pure mixture of methyl caprylate and methyl caprate;

b) reacting the purified methyl caprylate/caprate obtained from step a) with trimethylolpropane to transesterify the methyl caprylate/caprate; and c) removing methanol and unreacted methyl caprylate/caprate from the reaction mixture.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The mixture of methyl caprylate and methyl caprate used in step a) of the process of the invention can be readily obtained from naturally occurring oils, such as coconut oil and palm kernel oil. In fact, this methyl ester mixture can be obtained from the transesterification of triglycerides from the above oils with methyl alcohol, followed by distillation of the resulting fatty acid esters to produce a distillate fraction containing the caprylate and caprate methyl esters. This mixture is, however, not pure enough to use directly in step b) of the above process.

The mixture of methyl caprylate and methyl caprate usually has a molar ratio of about 60:40, although the molar ratio of the mixture is not critical and can vary from 10:90 to 90:10, preferably from 25:75 to 75:25 and more preferably from 35:65 to 65:35.

The mixture of methyl caprylate and methyl caprate can be purified in step a) by several different purification procedures, e.g., by (i) treatment with Attapulgus clay, (ii) treatment with Filtrol clays, (iii) acid wash using an aqueous mineral acid having a pH in the range of from 1 to 6, (iv) base wash using an aqueous alkali or alkaline earth metal carbonate or hydroxide, having a pH of from 8 to 14, or (v) a water wash followed by vacuum distillation of the washed mixture. The preferred method is procedure (v).

In step b) the purified mixture of methyl caprylate and methyl caprate is reacted with trimethylolpropane, preferably in the presence of a transesterification catalyst, such as butyl stannoic acid, dibutyltin diacetate, calcium acetate, sodium methoxide, and the like. The preferred catalyst for use in the present process is butyl stannoic acid.

Step b) is carried out using an excess, e.g., from 10% to 100% excess, preferably a 25% excess of the purified mixture of methyl esters in order to obtain the triester of trimethylolpropane, i.e., to obtain a hydroxyl value of less than 6, and preferably less than 4.

The reaction temperature in step b) can range from 150 to 250° C., preferably from 210 to 235° C.

During the course of the reaction in step b) methanol formed by the reaction is preferably removed continuously from the reaction mixture in order to shift the reaction equilibrium in favor of the trimethylolpropane caprylate/caprate product.

Step c) is preferably carried out by first vacuum distilling any remaining methanol and unreacted methyl caprylate and methyl caprate from the reaction mixture, until the above methyl esters are present in the reaction mixture at a concentration of not more than 3000 ppm, e.g., from 1000 to 3000 ppm.

Then steam distillation is carried out until the methyl ester content of the reaction mixture is reduced to less than 500 ppm. The recovered methyl esters can be recycled for use in the above process.

Following step c) the reaction mixture is dried under vacuum, and filtered.

The filtered reaction mixture can be further refined if desired by treatment with an aqueous solution of an alkali metal hydroxide, followed by water washing and vacuum drying.

The mixture of trimethylolpropane caprylate and trimethylolpropane caprate produced by the process of the invention can be used as a synthetic oil base for motor oils, either alone or in combination with other synthetic or hydrocarbon-based oils.

The product color, composition and physical properties of the present synthetic oil base meets or exceeds industrial product specifications.

The invention will be illustrated but not limited by the following example.

EXAMPLE

168 Grams of an unpurified mixture of methyl caprylate and methyl caprate (59:41 molar ratio) was treated with 2% by weight of Attapulgus clay by mixing in a beaker for 1 hour at 60° C. The resulting mixture was fltered through a Büchner funnel containing 11 $\mu$m filter paper and DICALITE™.

The filtrate was placed in a 3 liter, 4-neck flask equipped with a heating jacket, a thermostat control ($I^2R$ type), a mechanical stirrer and control, a Claisen head and H-trap decanter with a Friedrich condenser-vapor thermometer, and a subsurface $N_2$ inlet tube attached to an external nitrogen cylinder with gauge. Then 44.7 grams of trimethylolpropane, 0.7% by weight of carbon (DARKO™ KB), and 0.2% by weight of butyl stannoic acid catalyst (FASCAT™ 4100), were added to the flask.

The stirrer was turned on and the flask was heated with the heating jacket to a final temperature of 232° C. (reached after about 8 hours). At about 180° C. (pot temperature) methanol began to condense. A steady vapor temperature of 65–68° C. was maintained at the H-trap, while removing the methanol of reaction.

When the pot temperature reached 232° C. and the vapor temperature dropped below 40° C., a slow subsurface nitrogen purge was started (0.25 SCFH). A partial vacuum of about 10"–20" can also be applied to assist in completing the reaction.

When the hydroxyl value dropped to less than 6.0, the pot temperature was cooled to 190° C. The Claisen and H-trap were removed and replaced with a short path adaptor, a Friedrich condenser, a vacuum take-off to a 30", 2–5 torr vacuum pump, and a 500 ml receiver for stripping. Vacuum was applied slowly to a vacuum of 2 torr while maintaining a distillate rate of 1–2 drops/sec. When the hydroxyl value of the residue dropped below 4.0, the residue was steam stripped.

Steam stripping was carried out using a similar setup as in the above vacuum stripping, except that a larger receiver (2 liter flask) was used. The pot temperature was cooled to 160° C. and a 25" vacuum (90 torr) was applied and held for one hour while introducing live steam (about 3 ml/min.) subsurface to remove excess methyl esters to a value of less than 500 ppm. After one hour the steam was stopped and the contents dried under vacuum for one-half hour and then cooled to 60° C. 0.25% DICALITE™ was added, stirred for 2 minutes, and the resulting mixture was filtered through a Büchner funnel packed with a DICALITE™ bed. The filtrate was refiltered through the B4chner funnel.

What is claimed is:

1. A process for the preparation of a mixture of trimethylolpropane caprylate and trimethylolpropane caprate comprising the steps of
   A) purifying a less than pure mixture of methyl caprylate and methyl caprate;
   B) reacting the purified mixture from step A) with trimethylolpropane to transesterify the purified mixture to produce a reaction mixture containing trimethylolpropane caprylate and trimethylolpropane caprate; and
   C) removing methanol and unreacted methyl caprylate and methyl caprate from the reaction mixture.

2. The process of claim 1 wherein step A) is carried out by treatment with Attapulgus clay, by treatment with a Filtrol clay, by treatment with an acid or base, by water wash followed by vacuum distillation, or by a combination of two or more of the above procedures.

3. The process of claim 2 wherein the procedure used is a water wash followed by vacuum distillation.

4. The process of claim 1 where step B) is carried out in the presence of a transesterification catalyst.

5. The process of claim 4 wherein the transesterification catalyst is butyl stannoic acid, dibutyltin diacetate, calcium acetate, or sodium methoxide.

6. The process of claim 5 wherein said catalyst is butyl stannoic acid.

7. The process of claim 1 wherein in step B) a stoichiometric excess of the mixture of methyl esters is present based on the fully esterified trimethylolpropane.

8. The process of claim 1 wherein the mixture of methyl caprylate and methyl caprate has a mole ratio of from about 25:75 to about 75:25.

9. The process of claim 1 wherein step B) is carried out at a temperature in the range of from about 150 to about 250° C.

10. The process of claim 9 wherein said temperature is from about 210 to about 235° C.

11. The process of claim 1 where in step B) methanol when formed is continuously removed from the reaction mixture.

12. The process of claim 1 wherein step C) is carried out by vacuum distillation followed by steam distillation.

13. The process of claim 12 wherein following step C) the reaction mixture is dried under vacuum and filtered.

14. The process of claim 13 wherein following filtration the reaction mixture is treated with an alkali metal hydroxide.

15. The process of claim 1 wherein step A) is carried out by a water wash followed by vacuum distillation, step B) is carried out in the presence of butyl stannoic acid as a transesterification catalyst and with a stoichiometric excess of the mixture of methyl esters, and step C) is carried out by vacuum distillation followed by steam distillation.

16. A process for the preparation of a mixture of trimethylolpropane caprylate and trimethylolpropane caprate comprising the steps of:
   I) reacting a purified mixture of methyl caprylate and methyl caprate with trimethylolpropane to transesterify the purified mixture to produce a reaction mixture containing trimethylolpropane caprylate and trimethylolpropane caprate; and
   II) removing methanol and unreacted methyl caprylate and methyl caprate from the reaction mixture.

17. The process of claim 16 wherein step I) is carried out in the presence of a transesterification catalyst.

18. The process of claim 17 wherein the transesterification catalyst is butyl stannoic acid, dibutyltin diacetate, calcium acetate, or sodium methoxide.

19. The process of claim 18 wherein said catalyst is butyl stannoic acid.

20. The process of claim 18 wherein in step I) a stoichiometric excess of the mixture of methyl esters is present based on the fully esterified trimethylolpropane.

21. The process of claim 18 wherein the mixture of methyl caprylate and methyl caprate has a mole ratio of from about 25:75 to about 75:25.

22. The process of claim 18 wherein step B) is carried out at a temperature in the range of from about 150 to about 250° C.

23. The process of claim 22 wherein said temperature is from about 210 to about 235° C.

24. The process of claim 16 wherein in step I) methanol when formed is continuously removed from the reaction mixture.

25. The process of claim 16 wherein step II) is carried out by vacuum distillation followed by steam distillation.

26. The process of claim 25 wherein following step II) the reaction mixture is dried under vacuum and filtered.

27. The process of claim 26 wherein following filtration the reaction mixture is treated with an alkali metal hydroxide.

28. The process of claim 16 wherein step I is carried out in the presence of butyl stannoic acid as a transesterification catalyst and with a stoichiometric excess of the mixture of methyl esters, and step II) is carried out by vacuum distillation followed by steam distillation.

29. In a motor oil, the improvement wherein the motor oil base comprises the mixture of trimethylolpropane caprylate and trimethylolpropane caprate produced by the process of claim 16.

30. In a motor oil, the improvement wherein the motor oil base comprises the mixture of trimethylolpropane caprylate and trimethylolpropane caprate produced by the process of claim 28.

* * * * *